United States Patent
Motomura et al.

(10) Patent No.: US 9,476,807 B2
(45) Date of Patent: Oct. 25, 2016

(54) MICROPARTICLE SENSOR

(71) Applicant: NGK SPARK PLUG CO., LTD., Nagoya-shi, Aichi (JP)

(72) Inventors: Masayuki Motomura, Komaki (JP); Takeshi Sugiyama, Ichinomiya (JP); Keisuke Tashima, Kasugai (JP); Norimasa Osawa, Inuyama (JP); Toshiya Matsuoka, Gifu (JP); Hitoshi Yokoi, Aichi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 181 days.

(21) Appl. No.: 14/372,521

(22) PCT Filed: Feb. 13, 2013

(86) PCT No.: PCT/JP2013/000780
§ 371 (c)(1),
(2) Date: Jul. 16, 2014

(87) PCT Pub. No.: WO2013/125181
PCT Pub. Date: Aug. 29, 2013

(65) Prior Publication Data
US 2015/0020574 A1 Jan. 22, 2015

(30) Foreign Application Priority Data
Feb. 21, 2012 (JP) .................................. 2012-034611

(51) Int. Cl.
*G01N 27/70* (2006.01)
*G01N 1/22* (2006.01)
(Continued)

(52) U.S. Cl.
CPC .......... *G01N 1/2252* (2013.01); *G01M 15/102* (2013.01); *G01N 15/0656* (2013.01);
(Continued)

(58) Field of Classification Search
CPC .......... F01N 2560/05; G01N 33/0027; G01N 33/0036; G01N 2291/02408
See application file for complete search history.

(56) References Cited

U.S. PATENT DOCUMENTS 7,406,855 B2 * 8/2008 Tikkanen ............... G01N 27/62
73/23.31
7,609,068 B2 * 10/2009 Ripley ............... G01N 15/0656
324/500
(Continued)

FOREIGN PATENT DOCUMENTS

JP 2-19902 Y2 5/1990
JP 2007-514923 A 6/2007
(Continued)

OTHER PUBLICATIONS

International Search Report for PCT/JP2013/000780 dated Mar. 19, 2013.
(Continued)

*Primary Examiner* — Justin Olamit
(74) *Attorney, Agent, or Firm* — Sughrue Mion, PLLC

(57) ABSTRACT

A particulate sensor including a sensor unit (300) having an ion generation section (611, 361, 322); an electric charge section (612) for electrically charging at least portion of particulates S using ions PI; a capture section (616, 617, 316, 326, 362) for trapping at least portion of the ions PI not used for electrically charging the particulates S; and a sensor ground section (340, 310v, 330v3) connected to the capture section and having a first floating potential corresponding to the amount of the ions PI trapped by the capture section. The sensor unit can detect the amount of the particulates S in the gas on the basis of the electric potential of the sensor ground section. The sensor ground section is covered with insulating ceramic at that outer portion of the sensor unit which comes into contact with the gas.

6 Claims, 8 Drawing Sheets

(51) Int. Cl.
*G01N 33/00* (2006.01)
*G01N 15/06* (2006.01)
*G01M 15/10* (2006.01)

(52) U.S. Cl.
CPC ...... *G01N33/0027* (2013.01); *G01N 33/0036* (2013.01); *F01N 2560/02* (2013.01); *F01N 2560/05* (2013.01); *G01N 2291/02408* (2013.01)

(56) References Cited

U.S. PATENT DOCUMENTS

| | | | |
|---|---|---|---|
| 8,673,128 B2* | 3/2014 | Saitou | G01N 27/4077 |
| | | | 204/424 |
| 8,710,849 B2* | 4/2014 | Tikkanen | G01N 1/2252 |
| | | | 250/288 |
| 2006/0156791 A1 | 7/2006 | Tikkanen et al. | |
| 2010/0229632 A1 | 9/2010 | Tokuda et al. | |
| 2011/0050243 A1 | 3/2011 | Tikkanen | |
| 2012/0234172 A1 | 9/2012 | Sugiyama et al. | |
| 2012/0304738 A1 | 12/2012 | Landkammer | |

FOREIGN PATENT DOCUMENTS

| | | |
|---|---|---|
| JP | 2010-078429 A | 4/2010 |
| JP | 2010-210536 A | 9/2010 |
| JP | 2010-229957 A | 10/2010 |
| JP | 2011-513742 A | 4/2011 |
| JP | 2012-194078 A | 10/2012 |
| WO | 2009/109688 A1 | 9/2009 |
| WO | 2011/104426 A1 | 9/2011 |

OTHER PUBLICATIONS

Communication dated Mar. 3, 2015 from the Japanese Patent Office in counterpart application No. 2012-034611.

* cited by examiner

MICROPARTICLE SENSOR

CROSS REFERENCE TO RELATED APPLICATIONS

This application is a National Stage of International Application No. PCT/JP2013/000780 filed Feb. 13, 2013, claiming priority based on Japanese Patent Application No. 2012-034611, filed Feb. 21, 2012, the contents of all of which are incorporated herein by reference in their entirety.

TECHNICAL FIELD

The present invention relates to a sensor for detecting the amount of microparticles (particulates), such as soot, contained in exhaust gas.

BACKGROUND ART

Exhaust gas from an internal combustion engine such as a diesel engine contains particulates such as soot. In order to control or restrain the amount of particulates contained in exhaust gas which is exhausted from an internal combustion engine to the atmosphere, a particulate sensor for detecting the amount of particulates in exhaust gas may be attached to an exhaust gas pipe of the internal combustion engine. Such a particulate sensor is known to detect the amount of particulates in exhaust gas by generating ions through corona discharge, and electrically charging particles in exhaust gas by use of portion of the generated ions (Patent Document 1, etc., mentioned below).

The particulate sensor mentioned above has a floating potential section whose electric potential varies with the amount of ions used for electrically charging particulates, and a chassis ground section having the same chassis ground potential as that of piping such as a metal exhaust gas pipe to which the particulate sensor is attached. The particulate sensor detects current which flows between the floating potential section and the chassis ground section, thereby detecting the amount of particulates in exhaust gas. The floating potential section and the chassis ground potential section are electrically insulated with an insulating member at portions other than those used for detecting the current.

However, in a conventional particulate sensor, main components are composed of electrically conductive members, and these components vary in electric potential with the amount of ions used for electric charging. That is, the major components constitute a floating potential section. Furthermore, such electrically conductive members are partially exposed to the interior of the exhaust gas pipe. Thus, in the case of adhesion of particulates, water, oil, etc., contained in exhaust gas to that portion of the floating potential section which is exposed to the interior of the exhaust gas pipe, and to the exhaust gas pipe formed of an electrically conductive member, a short circuit is established therebetween. In such a condition, the electric potential of the floating potential section fails to accurately reflect the amount of ions used for electric charging. As a result, the particulate sensor fails to accurately detect the amount of particulates in exhaust gas.

Such a problem is widely involved in not only particulate sensors used for detecting soot in exhaust gas of internal combustion engines but also particulate sensors for detecting the amount of particulates in gas which contains particulates, through utilization of a configuration in which electric potential varies with the amount of ions used for electrically charging particulates or the amount of ions not used for electrically charging particulates.

PRIOR ART DOCUMENTS

Patent Documents

Patent Document 1: Japanese Kohyo (PCT) Patent Publication No. 2007-514923
Patent Document 2: International Publication WO2009/109688

SUMMARY OF THE INVENTION

Problem to be Solved by the Invention

An object of the present invention is to elongate service life of a particulate sensor for detecting the amount of particulates in gas which contains particulates, through utilization of a configuration in which electric potential varies with the amount of ions used for electrically charging particulates or the amount of ions not used for electrically charging particulates.

Means for Solving the Problem

The present invention has been conceived to solve, at least partially, the above problem and can be embodied in the following modes or application examples.

Application Example 1

A particulate sensor attached to a pipe having electrical conductivity, and adapted to detect the amount of particulates in gas flowing through the pipe, comprising a sensor unit, wherein
  the sensor unit comprises
  an ion generation section for generating ions,
  an electric charge section for electrically charging at least portion of the particulates in the gas which contains the particulates, by use of the ions,
  a capture section for trapping at least portion of the ions not used for electrically charging the particulates, and
  a sensor ground section connected to the capture section and having a first floating potential corresponding to the amount of the ions trapped by the capture section;
  the sensor unit can detect the amount of the particulates in the gas on the basis of electric potential of the sensor ground section; and
  the sensor ground section is covered with insulating ceramic at that outer portion of the sensor unit which comes into contact with the gas.

Application Example 2

A particulate sensor according to application example 1, wherein
  the ion generation section comprises a first electrode having a second floating potential different from the first floating potential, and a second electrode connected to the sensor ground section and having the first floating potential;
  the ion generation section generates the ions by producing discharge between the first electrode and the second electrode;
  the sensor unit further comprises a discharge potential portion connected to the first electrode and having the second floating potential; and the sensor ground section surrounds the first electrode and the discharge potential portion.

Application Example 3

A particulate sensor according to application example 2, comprising a structure formed of insulating ceramic and having the ion generation section, the electric charge section, the capture section, the sensor ground section, and the discharge potential portion, wherein the discharge potential portion is covered with the insulating ceramic used to form the structure; and the electric charge section is provided by the insulating ceramic used to form the structure.

Application Example 4

A particulate sensor according to application example 3, wherein the sensor unit further comprises a heater for heating the first and second electrodes and the capture section to a temperature capable of burning the particulates at the first and second electrodes and the capture section.

Application Example 5

A particulate sensor according to application example 4, wherein the sensor unit comprises the heater for heating the electric charge section to a temperature capable of burning the particulates at the electric charge section.

Application Example 6

A particulate sensor according to application example 4 or 5, further comprising a protector surrounding that outer portion of the structure which comes into contact with the gas, and allowing to pass therethrough the gas which contains the particulates.

The present invention can be embodied in various forms; for example, a sensor unit for use in a particulate sensor, an internal combustion engine having the sensor attached to an exhaust pipe, and a vehicle equipped with the internal combustion engine.

Effects of the Invention

Through employment of such a mode as application example 1, even when particulates in gas accumulate on that portion of the sensor unit which is in contact with the gas, the sensor ground section is not short-circuited to a pipe through which the gas flows, so that the sensor unit can accurately generate an output corresponding to the amount of ions used for electrically charging the particulates or the amount of ions not used for electrically charging the particulates. Thus, service life can be elongated for a particulate sensor which detects the amount of particulates in gas which contains the particulates, through utilization of a configuration in which output varies with the amount of ions used for electrically charging the particulates or the amount of ions not used for electrically charging the particulates.

In such a mode as application example 2, the sensor ground section forms a Faraday shield. Current which leaks from the first electrode and the discharge potential portion flows into the sensor ground section which surrounds the first electrode and the discharge potential portion. As a result, the sensor ground section can have an electric potential which accurately reflects the amount of ions trapped by the capture section. Thus, the particulate sensor can accurately detect the amount of particulates in gas on the basis of the potential of the sensor ground section.

Employment of such a mode as application example 3 can reduce the possibility of occurrence of a short circuit, caused by adhesion of particulates, etc., between electrically conductive members of the sensor unit, such as the sensor ground section and the discharge potential portion.

Employment of such a mode as application example 4 can prevent the occurrence of a situation in which the first and second electrodes and the capture section fail to sufficiently exhibit their functions as a result of accumulation of particulates thereon.

Employment of such a mode as application example 5 can prevent the occurrence of a situation in which the electric charge section fails to sufficiently exhibit its function as a result of accumulation of particulates on the structural surface of the electric charge section.

In a mode in which a protector as in the case of application example 6 is not provided, a structure whose temperature is increased by the heater may possibly be ruptured as a result of a locally abrupt temperature variation caused by adhesion of a water droplet on the heated structure. However, through employment of the above-mentioned mode, even when gas contains water droplets, there can be reduced the possibility of rupture of the structure caused by adhesion of a water droplet on the structure.

MODES FOR CARRYING OUT THE INVENTION

A. First Embodiment

A1. Configuration of Particulate Sensor

Figure 1:
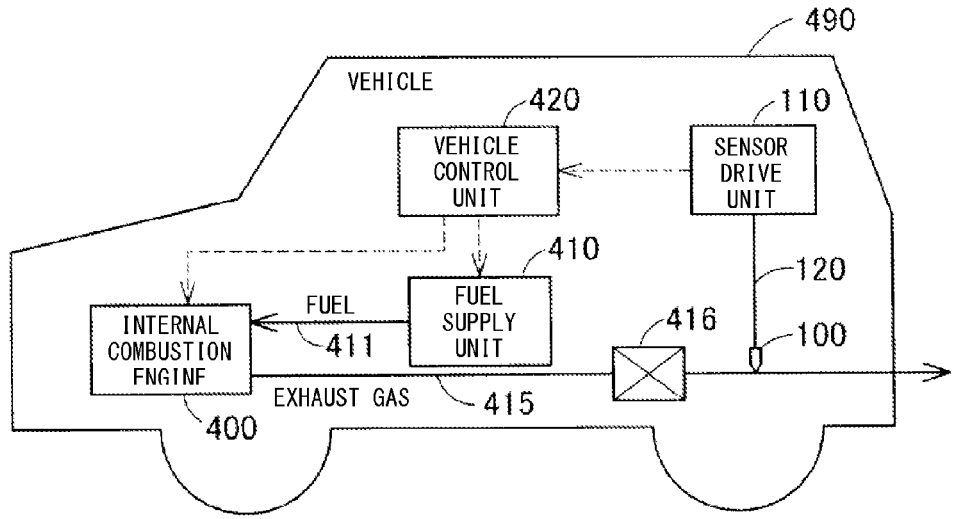
FIG. 1 A set of schematic views showing the configuration of a vehicle equipped with a particulate sensor, and the configuration of a sensor drive unit for controlling the particulate sensor.
Figure 1:
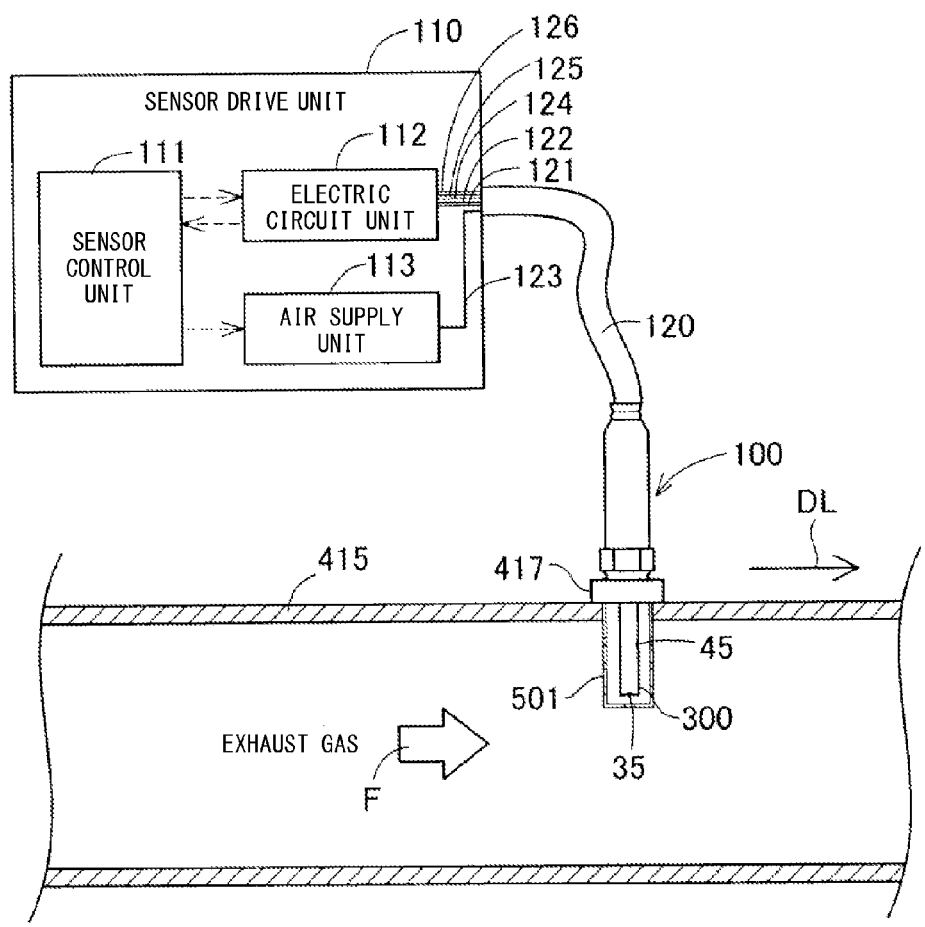

FIG. 1 is a set of schematic views showing the configuration of a vehicle equipped with a particulate sensor according to an embodiment of the present invention, and the configuration of a sensor drive unit for controlling the particulate sensor. As shown in FIG. 1(A), a vehicle 490 includes an internal combustion engine 400, a fuel supply unit 410, and a vehicle control unit 420. The internal combustion engine 400 is a power source of the vehicle 490 and can be, for example, a diesel engine.

The fuel supply unit 410 supplies fuel to the internal combustion engine 400 through a fuel pipe 411. An exhaust gas pipe 415 is connected to the internal combustion engine 400, and exhaust gas from the internal combustion engine 400 is discharged to the exterior of the vehicle 490 through the exhaust gas pipe 415. A filter device 416 (e.g., DPF (Diesel Particulate Filter): diesel particulate collection filter) for removing particulates such as soot contained in exhaust gas is provided in the exhaust gas pipe 415.

The vehicle control unit 420 is implemented by a microcomputer and controls the operating condition of the entire vehicle 490. Specifically, the vehicle control unit 420 controls the supply of fuel from the fuel supply unit 410 and the condition of combustion in the internal combustion engine 400.

The vehicle 490 is further equipped with a particulate sensor 100 and a sensor drive unit 110, which are shown in FIG. 1(B). The particulate sensor 100 is attached to the exhaust gas pipe 415 at a position located downstream of the filter device 416 and is connected to the sensor drive unit 110 through a cable 120.

The particulate sensor 100 is fixedly attached to the outer surface of the exhaust gas pipe 415 such that components thereof; specifically, a protector 501 and a portion of the sensor unit 300, are inserted into the interior of the exhaust gas pipe 415. More specifically, the particulate sensor 100 is attached to the outer surface of the exhaust gas pipe 415 through an attachment boss 417. The particulate sensor 100 is attached in such a manner that the rectangular columnar sensor unit 300 having a rectangular cross section is inserted into the exhaust gas pipe 415 substantially perpendicularly to an extending direction DL of the exhaust gas pipe 415 at an attachment position of the particulate sensor 100.

The sensor unit 300 has an intake hole 45 for introducing exhaust gas into the sensor unit 300, and a discharge hole 35 for discharging the introduced exhaust gas from the sensor unit 300, which will be described later in detail. In a state in which the sensor unit 300 is attached to the exhaust gas pipe 415, the intake hole 45 and the discharge hole 35 are located within the exhaust gas pipe 415. The sensor unit 300 measures a concentration of particulates contained in exhaust gas on the basis of the amount of particulates contained in the exhaust gas which is introduced therein through the intake hole 45. In the particulate sensor 100 of the present embodiment, the intake hole 45 is oriented downstream with respect to the flow of exhaust gas in the exhaust gas pipe 415. In FIG. 1, an arrow F indicates the direction of flow of exhaust gas.

A cable 120, which unitarily accommodates therein a plurality of electric wires 121, 122, 124, 125, and 126, an air supply tube 123, etc., is connected to a rear end portion (located opposite the sensor unit 300) of the particulate sensor 100. The other end of the cable 120 is connected to the sensor drive unit 110. Since the cable 120 is flexible, it can be run relatively freely in the vehicle 490.

The sensor drive unit 110 drives the particulate sensor 100 and detects the amount of particulates in exhaust gas on the basis of a detection signal from the particulate sensor 100. The amount of particulates in exhaust gas can be evaluated on the basis of, for example, the surface area of particulates or the mass of particulates. Alternatively, the amount of particulates in exhaust gas can also be evaluated on the basis of the number of particulates in a unit volume of exhaust gas. The sensor drive unit 110 is disposed away from the exhaust gas pipe 415.

The sensor drive unit 110 includes a sensor control unit 111, an electric circuit unit 112, and an air supply unit 113.

The sensor control unit 111 is implemented by a microcomputer. The sensor control unit 111 controls the electric circuit unit 112 and the air supply unit 113. Also, the sensor control unit 111 sends the vehicle control unit 420 the amount of particulates in exhaust gas detected by use of the particulate sensor 100 (see FIG. 1(A)).

The electric circuit unit 112 supplies electric power for driving the particulate sensor 100, through the insulated electric wires 121, 122, 125, and 126 accommodated in the cable 120. Also, the electric circuit unit 112 receives a sensor signal from the particulate sensor 100 through the signal line 124 accommodated in the cable 120. The electric circuit unit 112 sends the sensor control unit 111 the results of measurement based on the sensor signal.

The air supply unit 113 includes a pump (not illustrated). In response to an instruction from the sensor control unit 111, the air supply unit 113 supplies the particulate sensor 100 high-pressure air used for driving the particulate sensor 100, through the air supply tube 123 in the cable 120. The particulate sensor 100 may be supplied with a compressed gas other than air, through the air supply tube 123.

The vehicle control unit 420 shown in FIG. 1(A) can be configured such that, when the amount of particulates in exhaust gas received from the sensor control unit 111 (see FIG. 1(B)) is greater than a predetermined amount, a driver of the vehicle 490 is alarmed of deterioration or abnormality of the filter device 416. The vehicle control unit 420 can also be configured to adjust the condition of combustion in the internal combustion engine 400 on the basis of a detected value from the sensor control unit 111.

Figure 2:
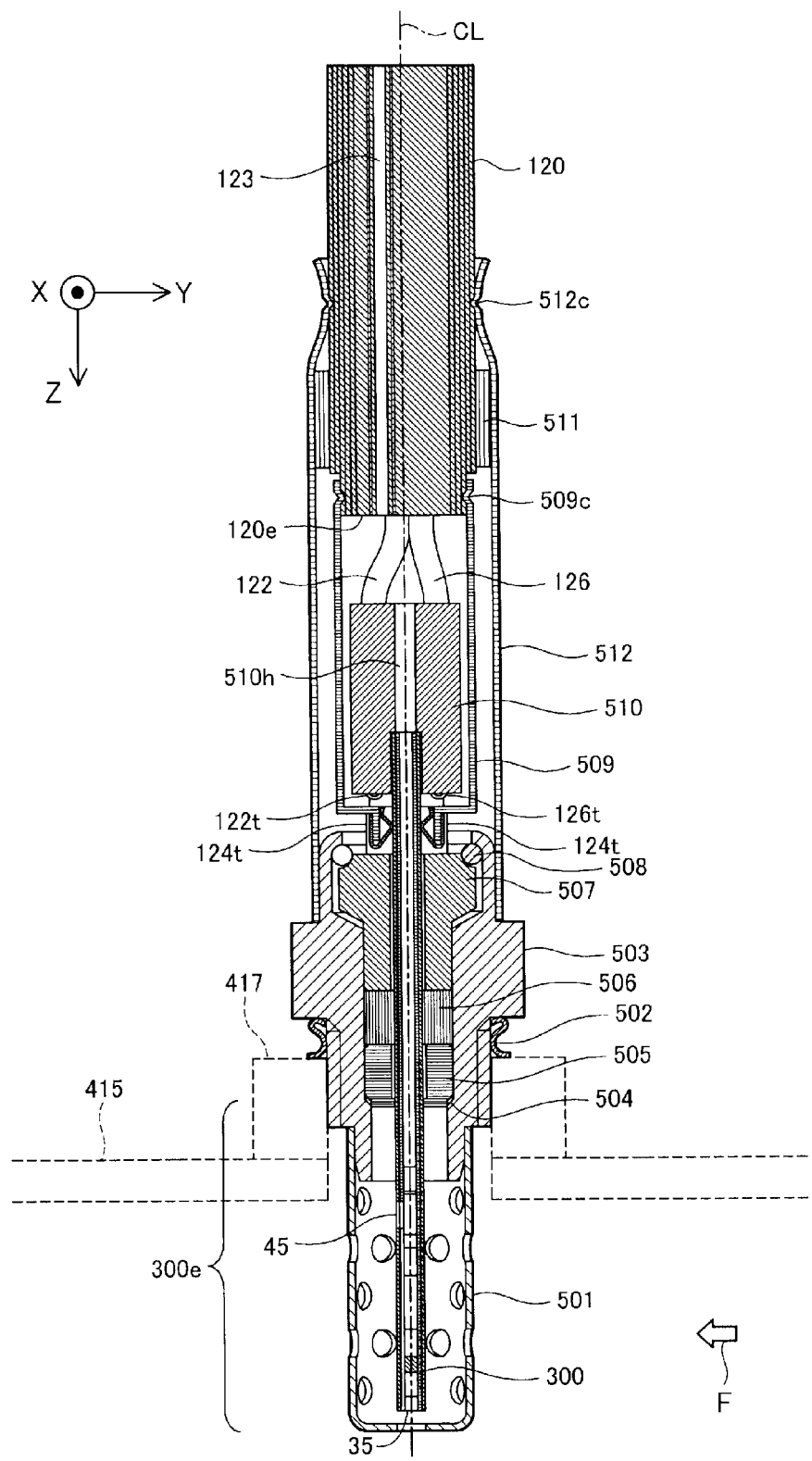
FIG. 2 Schematic sectional view showing the configuration of the particulate sensor.
Figure 3:
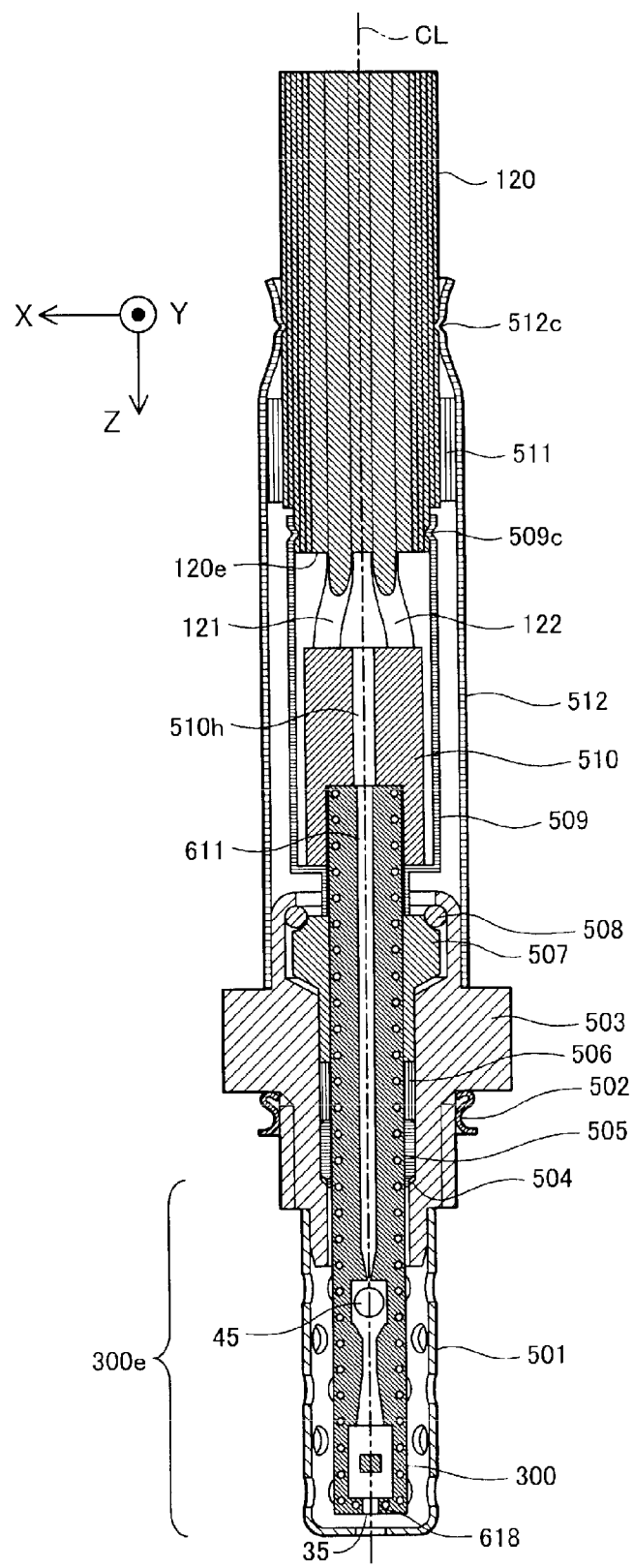
FIG. 3 Schematic sectional view showing the configuration of the particulate sensor.
Figure 4:
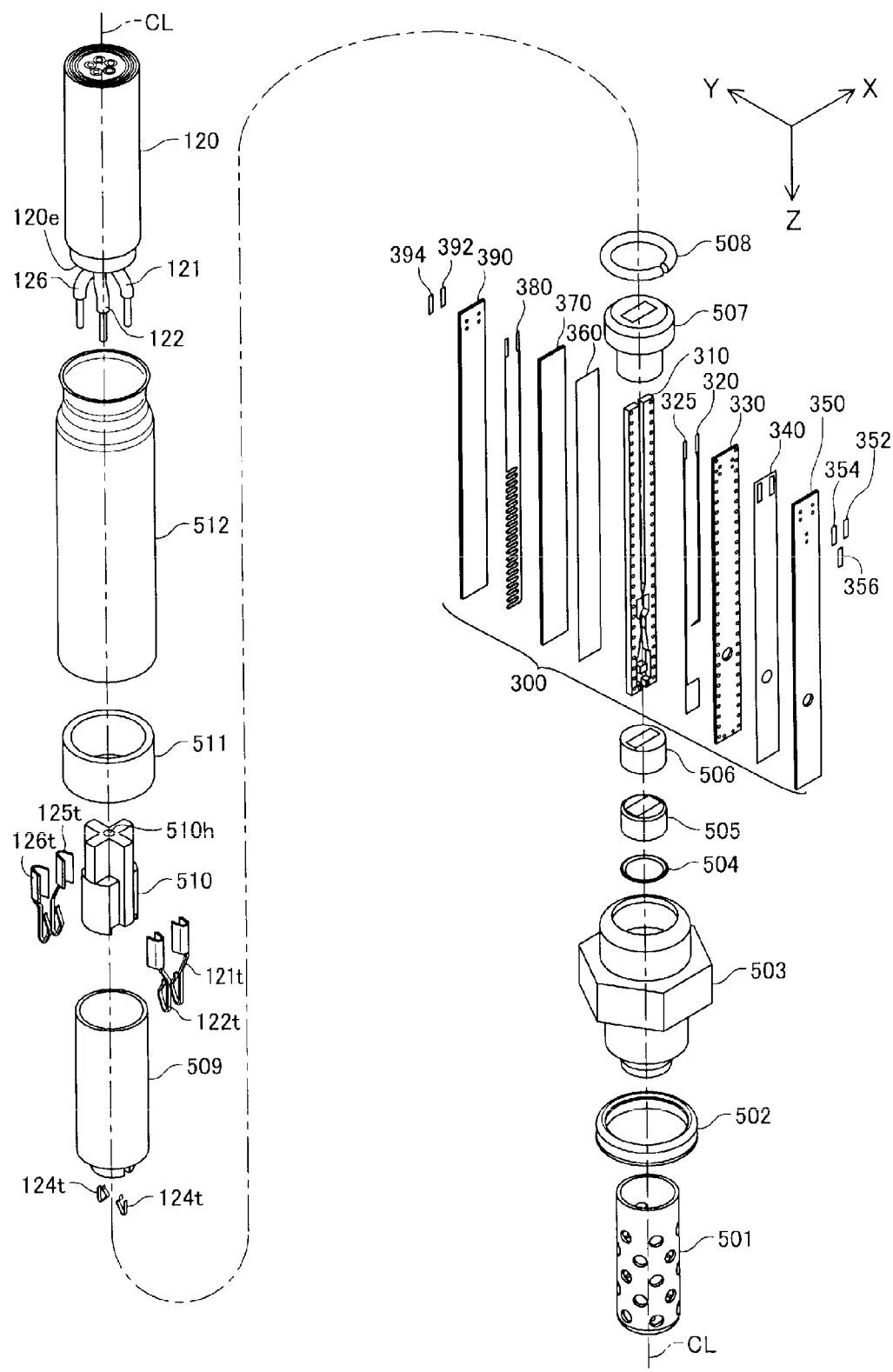
FIG. 4 Exploded perspective view showing the configuration of the particulate sensor.

FIGS. 2 and 3 are schematic sectional views of the particulate sensor 100 as viewed from directions which differ 90 degrees from each other. FIG. 4 is an exploded perspective view of the particulate sensor 100. FIGS. 2 to 4 show the particulate sensor 100 such that a side toward the sensor unit 300 (may be called merely a "forward side") is referred to as a lower side of paper on which the drawings appear and such that a side toward the cable 120 (may be called merely a "rear side") is referred to as an upper side of paper. In FIGS. 2 to 4, an imaginary center axis CL of the particulate sensor 100 is represented by the dot-dash line. For reference, FIG. 2 shows the exhaust gas pipe 415 and the attachment boss 417 illustrated in section by the broken line as viewed in a state in which the particulate sensor 100 is attached to the exhaust gas pipe 415. Also, the arrow F indicates the direction of flow of exhaust gas (see FIG. 1(B)).

FIGS. 2 to 4 further show arrows X, Y, and Z indicative of three-dimensional axes for indicating orientational correspondence among the drawings. Specifically, the arrow Z indicates a direction along the imaginary center axis CL of the particulate sensor 100 and indicates a downward direction on paper on which the drawings appear. The arrow Y indicates a direction opposite the direction in which the intake hole 45 opens. The arrow Y indicates a rightward direction on paper on which FIG. 2 appears, a direction toward the near side with respect to paper on which FIG. 3 appears, and an upper leftward direction on paper on which FIG. 4 appears. The arrow X indicates a direction perpendicular to the arrow Z and along the opening plane of the intake hole 45. The arrow X indicates a direction toward the near side with respect to paper on which FIG. 2 appears, a leftward direction on paper on which FIG. 3 appears, and an upper rightward direction on paper on which FIG. 4 appears.

Components of the particulate sensor 100 will next be described. However, the sequence of description of the components does not indicate the sequence of attachment of the components in the manufacturing process of the particulate sensor 100.

The particulate sensor 100 has the substantially rectangular columnar sensor unit 300 formed of insulating ceramic (see the lower regions in FIGS. 2 and 3 and the right middle region in FIG. 4). The sensor unit 300 is inserted through a cylindrical talc (talc ring) 506 having a substantially rectangular hole. While being disposed in a metallic shell 503 and around the sensor unit 300 at a predetermined position, the talc 506 is compressed forward with respect to the imaginary center axis CL, whereby the talc 506 is compressed in a filling manner between the inner circumferential surface of the metallic shell 503 and the outer circumferential surface of the sensor unit 300 and thus airtightly holds the sensor unit 300 to the metallic shell 503. A cylindrical first ceramic ring 505 having a substantially rectangular hole is disposed forward of the talc 506. That portion 300e of the sensor unit 300 which is located forward of the first ceramic ring 505 comes into contact with exhaust gas flowing through the exhaust gas pipe 415 (see the lower region in FIG. 2).

A stepped cylindrical second ceramic ring 507 having a substantially rectangular hole is disposed rearward of the talc 506. The first ceramic ring 505 and the second ceramic ring 507 are formed of insulating ceramic such as alumina. The sensor unit 300 extends through the substantially rectangular holes formed in the talc 506, the first ceramic ring 505, and the second ceramic ring 507.

The first ceramic ring 505, the talc 506 which holds the sensor unit 300, and the second ceramic ring 507 are disposed in a stepped cylindrical hole which is provided in the metallic shell 503 and whose diameter reduces forward in a sequentially stepped manner (see the lower regions in FIGS. 2 and 3 and the lower right region in FIG. 4). An annular sheet packing 504 is disposed between the first ceramic ring 505 and a step in the hole of the metallic shell 503.

The metallic shell 503 has a substantially three-stepped cylindrical outline whose outside diameter increases rearward in a sequentially stepwise manner and has a hexagonal columnar flange provided between the second and third cylinders and having a radial size greater than the outside diameter of the third cylinder. A thread is formed on the outer surface of the second thinnest cylinder for threadingly attaching the metallic shell 503 and, in turn, the particulate sensor 100 into the attachment boss 417 (see the lower region in FIG. 2). The axis of the stepped cylindrical hole of the metallic shell 503 coincides with the axis of the stepped cylindrical outline of the metallic shell 503. Since the metallic shell 503 has electrical conductivity, and the attachment boss 417 also has electrical conductivity, the metallic shell 503 has the electric potential of the chassis ground, which is the ground of the vehicle 490.

A cylindrical protector 501 having a forward end bottom is externally fitted to the thinnest forward end cylinder of the metallic shell 503. A forward end portion of the sensor unit 300 protrudes forward from the metallic shell 503 and is located within the cylindrical protector 501 (see the lower regions in FIGS. 2 and 3). The protector 501 is disposed such that the center axis of the cylinder of the protector 501 coincides with the imaginary center axis CL.

The protector 501 has a plurality of communication holes formed in its side wall. The protector 501 also has a communication hole formed in its bottom at a position located on the center axis of the cylinder. These communication holes have such a size and shape as to allow passage therethrough of exhaust gas which contain soot to be detected by the particulate sensor 100. An annular gasket 502 is externally attached to the second thinnest cylinder of the metallic shell 503 at the boundary to the hexagonal columnar flange.

An arcuate line packing 508 is disposed rearward of the second ceramic ring 507 (see the middle regions in FIGS. 2 and 3 and the upper right region in FIG. 4) in the stepped hole of the metallic shell 503. The line packing 508, the first ceramic ring 505, the talc 506, and the second ceramic ring 507 are disposed in the stepped cylindrical hole of the metallic shell 503. The rear end of the third cylinder of the metallic shell 503 is crimped radially inward, whereby the sheet packing 504, the first ceramic ring 505, the talc 506, the second ceramic ring 507, and the line packing 508 are fixed within the metallic shell 503; as a result, the sensor unit 300 is fixed to the metallic shell 503.

A separator 510 is disposed rearward of the sensor unit 300 (see the middle regions in FIGS. 2 and 3 and the lower left region in FIG. 4). The separator 510 has a substantially rectangular columnar recess formed at the forward end thereof, and the rear end of the sensor unit 300 is fitted into the recess. The separator 510 is a columnar member having a cross-shaped cross section. The separator 510 is disposed such that its axis coincides with the imaginary center axis CL of the particulate sensor 100. The separator 510 has a through hole 510h whose axis coincides with the axis of a column thereof. The through hole 510h is connected, at its forward end, to the substantially rectangular columnar recess mentioned above. A forward portion of the cross-shaped outline of the separator 510 where the substantially rectangular columnar recess is provided is thicker than a rear portion of the cross-shaped outline.

Four spaces which are mutually separated by the walls which constitute the substantially cross-shaped cross section of the separator 510 receive distal end portions of the insulated electric wires 121, 122, 125, and 126, respectively, of the cable 120 (see FIG. 4). At a distal end portion of the cable 120, an outer component part of the cable 120 is removed, and the insulated electric wires 121, 122, 125, and 126 are exposed. Terminals 121t, 122t, 125t, and 126t are attached to distal end portions of the insulated electric wires 121, 122, 125, and 126, respectively (see the middle region in FIG. 2 and the lower left region in FIG. 4). Forward portions of the terminals 121t, 122t, 125t, and 126t are located forward of the separator 510. The forward portions of the terminals 121t, 122t, 125t, and 126t are in contact with respective electrode pads provided on the front and back surfaces of the sensor unit 300 (see the middle region in FIG. 2).

The separator 510 and the terminals 121t, 122t, 125t, and 126t are accommodated in a stepped cylindrical inner tube 509 whose diameter reduces forward in a stepped manner (see the middle regions in FIGS. 2 and 3 and the lower left region in FIG. 4). The sensor unit 300 passes through a thinner cylinder of the inner tube 509 and reaches the interior of the substantially rectangular columnar recess of the separator 510. The inner tube 509 has electrical conductivity. A pair of terminals 124t is attached to the forward-end thinner cylinder of the inner tube 509 (see the middle region in FIG. 2 and the lower left region in FIG. 4). The pair of terminals 124t holds the sensor unit 300 from opposite sides. One of the two terminals 124t is in contact with an electrode pad provided on the surface of the sensor unit 300.

The inner tube 509 is crimped, at its rear end portion, to the cable 120 whose two outer layers are removed. A crimped portion 509c is shown in the upper regions in FIGS.

2 and 3. The crimped portion 509c of the inner tube 509 penetrates through the third layer counted from the outside of the cable 120 and electrically communicates with the fourth layer; i.e., a first shield line SL1 (see FIG. 5). The first shield line SL1 functions as a signal line 124 (see FIG. 1(B)) for transmitting signals between the electric circuit unit 112 and the particulate sensor 100.

An outer tube 512 connects the cable 120 and the exterior of the rearmost (third) cylinder of the metallic shell 503. That is, a forward end portion of the outer tube 512 is fitted to the exterior of the rearmost cylinder of the metallic shell 503. A rear end portion of the outer tube 512 is crimped to the cable 120. A crimped portion 512c is shown in the upper regions in FIGS. 2 and 3. The outer layer of the cable 120 remains intact at that portion of the cable 120 to which the rear end portion of the outer tube 512 is crimped. The crimped portion 512c of the outer tube 512 penetrates through the outermost layer of the cable 120 and electrically communicates with the second layer counted from the outside of the cable 120; i.e., a second shield line SL2 (see FIG. 5). As a result, the second shield line SL2 electrically communicates with the metallic shell 503, the exhaust gas pipe 415, etc., through the outer tube 512 and thus has the potential of the chassis ground.

As shown in the upper region in FIG. 2, the air supply tube 123 (see FIG. 1(B)) opens at an end surface 120e of the cable 120 where the insulated electric wires 121, 122, 125, and 126 are exposed. As a result, compressed air supplied from the air supply tube 123 fills the inner tube 509 and is supplied toward the sensor unit 300 through the through hole 510h of the separator 510. Compressed air supplied from the air supply tube 123 also fills the interior of the outer tube 512 through an opening in the bottom of the inner tube 509. However, the rear end of the space within the outer tube 512 is substantially sealed up by a grommet 511 and the crimped portion 512c, and the forward end of the space is sealed up by the metallic shell 503, the talc 506, and the sheet packing 504. Thus, most compressed air is supplied to the sensor unit 300 through the through hole 510h of the separator 510.

Figure 5:
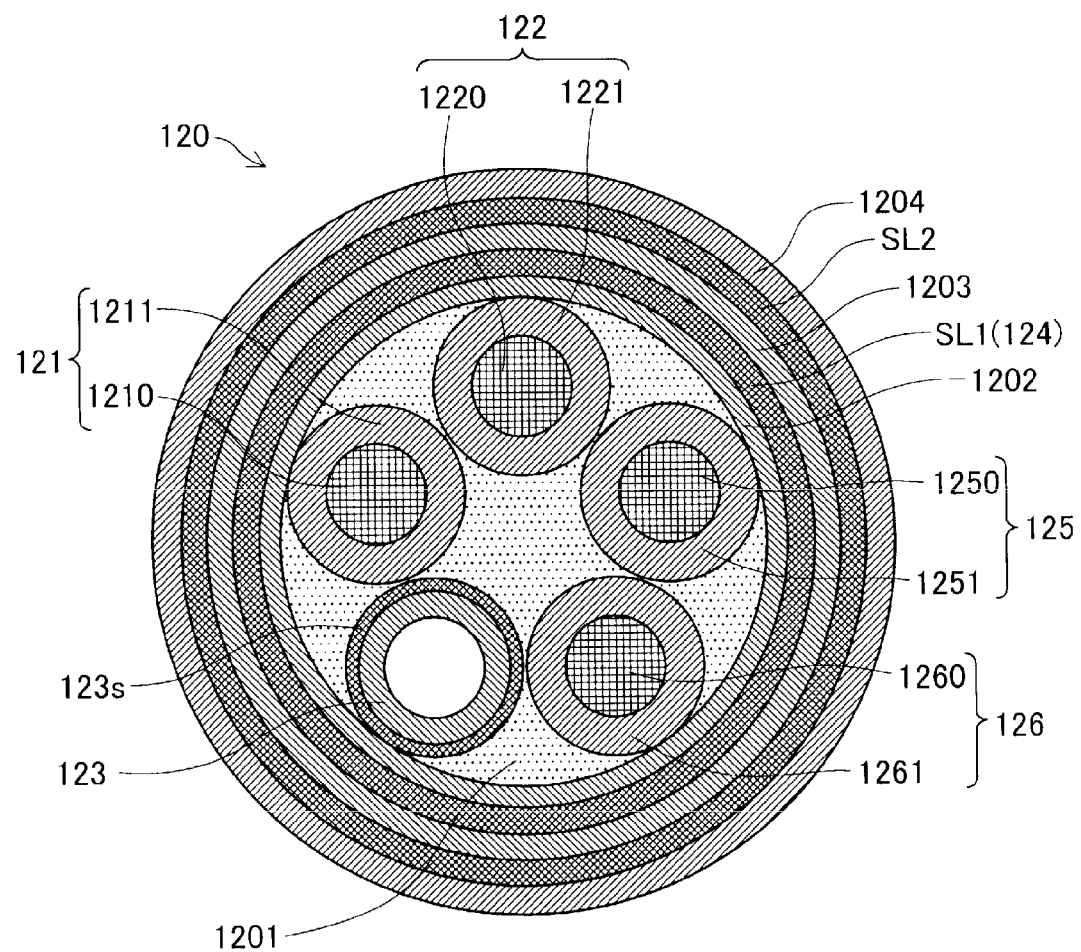
FIG. 5 Schematic sectional view showing the configuration of a cable connected to the particulate sensor.

FIG. 5 is a schematic sectional view showing the configuration of the cable 120 connected to the particulate sensor 100 of the present embodiment. The cable 120 unitarily accommodates the first insulated electric wire 121, the second insulated electric wire 122, the third insulated electric wire 125, the fourth insulated electric wire 126, the air supply tube 123, and the signal line 124 (see also FIG. 1(B)). Such a configuration facilitates the running of the tube and the electric wires connected to the particulate sensor 100. Thus, the particulate sensor 100 can be readily mounted in the vehicle 490.

The first insulated electric wire 121 has, at its center, a core wire 1210 which is an electrically conductive wire. The core wire 1210 is covered with a resin coating layer 1211. The second to fourth insulated electric wires 122, 125, and 126 are also similarly configured. Core wires 1220, 1250, and 1260 and resin coating layers 1221, 1251, and 1261 are shown in FIG. 5.

By use of the sectional view of the cable 120 shown in FIG. 5, the configurations of the first to fourth insulated electric wires 121, 122, 125, and 126 have been described. However, those portions of the first to fourth insulated electric wires 121, 122, 125, and 126 which are not covered with a glass fiber filler 1201 and with the outer layers and are thus exposed (see the intermediate regions in FIGS. 2 and 3 and the upper left region in FIG. 4) have the respective coating layers as mentioned above.

The air supply tube 123 shown in FIG. 5 is formed by a tubular resin member. The outer circumference of the air supply tube 123 is covered with a reinforcement member 123s. Preferably, the reinforcement member 123s has flexibility and is higher in rigidity than the resin member; for example, the reinforcement member 123s can be formed by braiding a metal wire. Even when the resin member used to form the air supply tube 123 is softened to no small extent as a result of increase in temperature, the reinforcement member 123s restrains expanded deformation of the air supply tube 123 which could otherwise be caused by air pressure. That is, through use of the cable 120, air having higher pressure can be supplied to the particulate sensor 100 even in high-temperature environment.

A space around the insulated electric wires 121, 122, 125, and 126 and the reinforcement member 123s of the air supply tube 123 is filled with glass fiber, thereby forming the glass fiber filler 1201. The glass fiber filler 1201 is covered with a first cable coating layer 1202. The first cable coating layer 1202 can be formed of resin.

The first shield line SL1 formed by braiding an electrically conductive wire is disposed around the outer circumference of the first cable coating layer 1202. A second cable coating layer 1203 formed of resin is provided externally of the first shield line SL1. Furthermore, the second shield line SL2 formed by braiding an electrically conductive wire is disposed around the outer circumference of the second cable coating layer 1203. The outer circumference of the second shield line SL2 is covered with a covering 1204 formed of resin.

As mentioned above, the first shield line SL1 is electrically connected to the sensor unit 300 through the inner tube 509 (see the middle regions in FIGS. 2 and 3). Through employment of such a configuration, as mentioned above, the first shield line SL1 functions as the signal line 124 which connects the electric circuit unit 112 and the sensor unit 300 of the particulate sensor 100.

Meanwhile, as mentioned above, the second shield line SL2 electrically communicates with the outer tube 512 (see the upper regions in FIGS. 2 and 3). As a result, the second shield line SL2 is electrically connected to the chassis (not shown) of the vehicle 490 through the outer tube 512, the metallic shell 503, the attachment boss 417, and the exhaust gas pipe 415. As a result, the second shield line SL2 is grounded.

Figure 6:
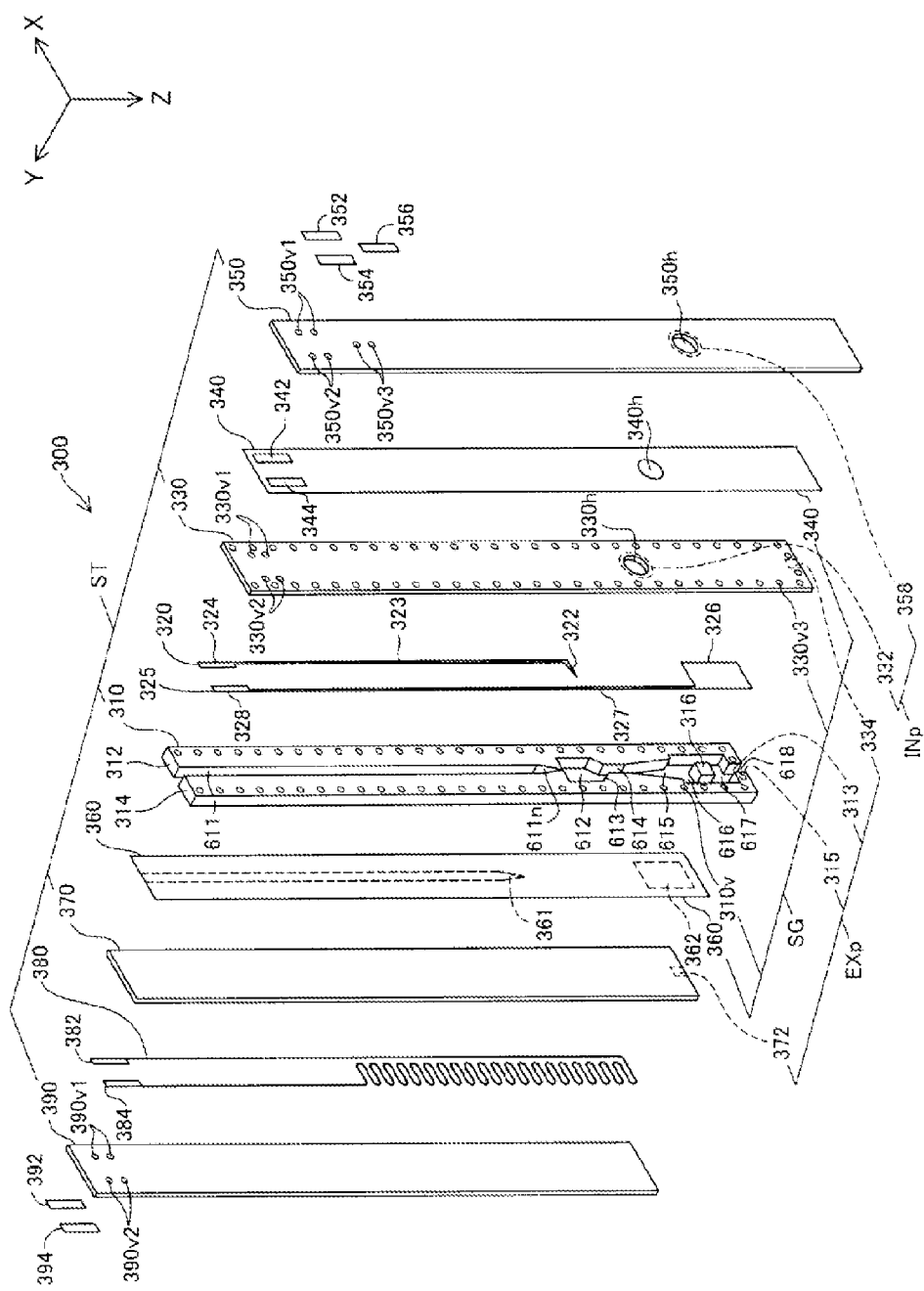
FIG. 6 Exploded perspective view showing the configuration of a sensor unit.

FIG. 6 is an exploded perspective view showing the configuration of the sensor unit 300. FIG. 6 also shows the three-dimensional axes X, Y, and Z for indicating orientational correspondence to FIGS. 2 to 4. In FIG. 6, the arrow X indicates an upper rightward direction on paper on which the drawing appears; the arrow Y indicates an upper leftward direction on paper on which the drawing appears; and the arrow Z indicates a direction along the imaginary center axis CL of the particulate sensor 100 (see FIGS. 2 to 4).

A first ceramic layer 310 is provided at the center of the sensor unit 300. The first ceramic layer 310 includes a pair consisting of outer peripheral portions 312 and 314, and a columnar portion 316 disposed between the outer peripheral portions 312 and 314.

The pair consisting of the outer peripheral portions 312 and 314 having line-symmetrical shapes defines, within the sensor unit 300, a channel through which high-pressure air, ions, and exhaust gas flow. The channel is formed between the outer peripheral portion 312 and the outer peripheral portion 314. Fluid such as exhaust gas flows the top to the bottom in FIG. 6; more specifically, fluid flows through the channel from the rear side toward the forward side of the particulate sensor 100. The pair consisting of the outer peripheral portions 312 and 314 is formed and disposed in such a manner as to collectively form a substantially rectangular shape.

The channel formed between the outer peripheral portion 312 and the outer peripheral portion 314 is composed of channels 611 to 618 arranged sequentially from the rear side to the forward side of the sensor unit 300. The channels 611 to 618 are formed in such a manner as to contain the imaginary center axis CL of the particulate sensor 100 (see FIG. 4). The channels 611 to 618 are "inner spaces" of the sensor unit 300.

The rear end of the channel 611 is connected to the through hole 510$h$ of the separator 510 (see the middle region in FIG. 2 and the lower left region and the upper right region in FIG. 4). The channel 611 receives compressed air through the through hole 510$h$ of the separator 510. The compressed air flows through the channels 611 to 618 and is discharged, together with exhaust gas, from the discharge hole 35 provided at the forward end of the sensor unit 300 (see the lower region in FIG. 3). The downstream end opening of the channel 618 is the discharge hole 35. A forward end portion 611$n$ of the channel 611 is formed such that its cross-sectional area reduces along the direction of flow. That is, the forward end portion 611$n$ of the channel 611 functions as a nozzle (orifice). The columnar portion 316 is disposed at a connection between the channel 616 and the channel 617 and hinders a rectilinear forward flow of compressed air. The function of the columnar portion 316 will be described later.

As shown in FIG. 6, a discharge pattern 320 and a trap pattern 325 are disposed on the Y-axis negative side (hereinafter, called the "front side") with respect to the first ceramic layer 310. In actuality, the discharge pattern 320 and the trap pattern 325 are formed through pattern-printing on the Y-axis front side surface of a second ceramic layer 330. A distal end portion 322 of the discharge pattern 320 is located on the forward end portion 611$n$ of the channel 611 and functions as one of two discharge electrodes. Hereinafter, the distal end portion 322 of the discharge pattern 320 may be referred to as the "first electrode 322." A portion 323 other than the distal end portion 322 of the discharge pattern 320 is disposed on the outer peripheral portion 312 of the first ceramic layer 310.

A distal end portion 326 of the trap pattern 325 is located on the channels 616 and 617 which partially constitute a trap, and functions similarly as a portion of the capture section. A portion 327 other than the distal end portion 326 of the trap pattern 325 is disposed on the outer peripheral portion 314 of the first ceramic layer 310.

The second ceramic layer 330 is disposed on the front side with respect to the discharge pattern 320 and the trap pattern 325. The second ceramic layer 330 has a substantially rectangular outline which matches the overall outline of the outer peripheral portions 312 and 314 when projected in the Y-axis direction. The second ceramic layer 330 has an opening 330$h$ located above the channel 612 which functions as a mixer. The opening 330$h$ functions as a portion of the intake hole 45 for introducing exhaust gas into the sensor unit 300 (see FIG. 1(B) and the lower regions in FIGS. 2 and 3).

The discharge pattern 320 and the trap pattern 325 are covered with the second ceramic layer 330. More specifically, the portion 323 other than the distal end portion 322 of the discharge pattern 320 and the portion 327 other than the distal end portion 326 of the trap pattern 325 are sandwiched between and thus covered with the first ceramic layer 310 and the second ceramic layer 330. As a result, the portion 323 of the discharge pattern 320 and the portion 327 of the trap pattern 325 are not exposed to the channels 611 to 618. The discharge pattern 320 and the trap pattern 325 are not exposed to the outside of the sensor unit 300. In an actual manufacturing process, as mentioned above, for example, the discharge pattern 320 and the trap pattern 325 are provided beforehand, through pattern-printing, on the surface of the second ceramic layer 330 which faces the first ceramic layer 310.

A first ground pattern 340 is disposed on the front side with respect to the second ceramic layer 330. The first ground pattern 340 has a substantially rectangular outline smaller than the outline of the second ceramic layer 330. The first ground pattern 340 is disposed at such a position as to fall within the region of the second ceramic layer 330 when projected in the Y-axis direction.

The first ground pattern 340 has an opening 340$h$ located above the channel 612 which functions as a mixer. The opening 340$h$ is disposed at such a position as to align with the opening 330$h$ of the second ceramic layer 330 when projected in the Y-axis direction. However, the opening 340$h$ is greater than the opening 330$h$. The opening 340$h$, together with the opening 330$h$, functions as a portion of the intake hole 45 (see FIG. 1(B) and the lower regions in FIGS. 2 and 3). The first ground pattern 340 has an opening 342 at such a position as to be superimposed on a rear end portion 324 of the discharge pattern 320 when projected in the Y-axis direction. Additionally, the first ground pattern 340 has an opening 344 at such a position as to be superimposed on a rear end portion 328 of the trap pattern 325 when projected in the Y-axis direction.

A third ceramic layer 350 is disposed on the front side with respect to the first ground pattern 340. The third ceramic layer 350 has a substantially rectangular outline which matches the outline of the second ceramic layer 330 when projected in the Y-axis direction. The third ceramic layer 350 has an opening 350$h$ located above the channel 612 which functions as a mixer. The opening 350$h$ is disposed at such a position as to align with the opening 330$h$ of the second ceramic layer 330 and with the opening 340$h$ of the first ground pattern 340 when projected in the Y-axis direction. However, the opening 350$h$ is smaller than the opening 340$h$. The opening 350$h$, together with the openings 330$h$ and 340$h$, functions as a portion of the intake hole 45 (see FIG. 1(B) and the lower regions in FIGS. 2 and 3).

The first ground pattern 340, including an end plane of the opening 340$h$, is covered with the third ceramic layer 350. That is, the first ground pattern 340 is sandwiched between and covered with the second ceramic layer 330 and the third ceramic layer 350. As a result, the first ground pattern 340 is not exposed to the channels 611 to 618 and to the exterior of the sensor unit 300.

The second ceramic layer 330 and the third ceramic layer 350 have two vias 330$v$1 and two vias 350$v$1, respectively, at such positions as to be superimposed on the rear end portion 324 of the discharge pattern 320 when projected in the Y-axis direction. The vias 330$v$1 extend through the second ceramic layer 330. The vias 350$v$1 extend through the third ceramic layer 350. The two vias 330$v$1 and two vias 350$v$1 are filled with electrically conductive members, respectively. The electrically conductive members extend through the opening 342 of the first ground pattern 340 while being electrically insulated from the first ground pattern 340, and electrically communicate with the rear end portion 324 of the discharge pattern 320. Furthermore, an electrode pad 352 is provided on the front side of the third ceramic layer 350 and electrically communicates with the vias 350v1.

The terminal 121t connected to the insulated electric wire 121 is in contact with the electrode pad 352 (see the lower left region in FIG. 4). The discharge pattern 320 is supplied with electric power from the electric circuit unit 112 (see FIG. 1(B)) through the insulated electric wire 121, the terminal 121t, the electrode pad 352, and the vias 350v1 and 330v1.

Similarly, the second ceramic layer 330 and the third ceramic layer 350 have two vias 330v2 and two vias 350v2, respectively, at such positions as to be superimposed on the rear end portion 328 of the trap pattern 325 when projected in the Y-axis direction. The vias 330v2 extend through the second ceramic layer 330. The vias 350v2 extend through the third ceramic layer 350. The two vias 330v2 and two vias 350v2 are filled with electrically conductive members, respectively. The electrically conductive members extend through the opening 344 of the first ground pattern 340 while being electrically insulated from the first ground pattern 340, and electrically communicate with the rear end portion 328 of the trap pattern 325. Furthermore, an electrode pad 354 is provided on the front side of the third ceramic layer 350 and electrically communicates with the vias 350v2.

The terminal 122t connected to the insulated electric wire 122 is in contact with the electrode pad 354 (see the middle region in FIG. 2 and the lower left region in FIG. 4). The trap pattern 325 is supplied with electric power from the electric circuit unit 112 (see FIG. 1(B)) through the insulated electric wire 122, the terminal 122t, the electrode pad 354, and the vias 350v2 and 330v2.

Furthermore, the third ceramic layer 350 has two vias 350v3 at such positions as to be superimposed on the first ground pattern 340 when projected in the Y-axis direction. The vias 350v3 extend through the third ceramic layer 350. The vias 350v3 are filled with electrically conductive members, respectively. The electrically conductive members electrically communicate with the first ground pattern 340. An electrode pad 356 is provided on the front side of the third ceramic layer 350 and electrically communicates with the vias 350v3.

The terminal 124t which is connected to the signal line 124 (first shield line SL1) through the electrically conductive inner tube 509, etc., is in contact with the electrode pad 356 (see the middle region in FIG. 2 and the lower left region in FIG. 4). The electric potential of the first ground pattern 340 is transmitted to the electric circuit unit 112 of the sensor drive unit 110 through the via 350v3, the electric pad 356, the terminal 124t, the inner tube 509 and other members, and the signal line 124.

In a state in which the sensor unit 300 is incorporated in the particulate sensor 100, the electrode pads 352, 354, and 356 are located rearward of the metallic shell 503 and the second ceramic ring 507 (see the middle right region in FIG. 4 and the middle region in FIG. 3). Thus, the electrode pads 352, 354, and 356 are in noncontact with exhaust gas.

Meanwhile, as shown in FIG. 6, a second ground pattern 360 is disposed on the Y-axis positive side (hereinafter, called the "back side") with respect to the first ceramic layer 310. The second ground pattern 360 has a substantially rectangular outline smaller than the substantially rectangular overall outline of the outer peripheral portions 312 and 314 of the first ceramic layer 310 when projected in the Y-axis direction. The second ground pattern 360 is disposed at such a position as to be contained in the substantially rectangular outline of the outer peripheral portions 312 and 314 when projected in the Y-axis direction. The second ground pattern 360 is exposed to the channels 611 to 618 and forms a bottom for the channels 611 to 618.

A fourth ceramic layer 370 is disposed on the back side with respect to the second ground pattern 360. The fourth ceramic layer 370 has a substantially rectangular outline which matches the substantially rectangular overall outline of the outer peripheral portions 312 and 314 when projected in the Y-axis direction.

The second ground pattern 360 is covered with the fourth ceramic layer 370. That is, the second ground pattern 360 is sandwiched between and thus covered with the first ceramic layer 310 and the fourth ceramic layer 370. As a result, the second ground pattern 360 is not exposed to the exterior of the sensor unit 300.

A heater pattern 380 is disposed on the back side with respect to the fourth ceramic layer 370. The heater pattern 380 is a continuous electric heating wire pattern having opposite ends on the rear-end side of the sensor unit 300. Through reception of supplied electric power, the heater pattern 380 heats the entire sensor unit 300, encompassing the second electrode 362 of the second ground pattern 360, the distal end portion 326 of the trap pattern 325, and the first electrode 322 of the discharge pattern 320, to a temperature of 550 to 600 degrees. As a result, there is burned soot adhering to that portion of the second ground pattern 360 which is exposed to the channels 611 to 618, to the distal end portion 326 exposed to the channels 616 and 617, to the first electrode 322 exposed to the channel 613, etc. Thus, such components are not covered with soot and thus can exhibit performance over a long period of time.

Preferably, platinum is used to form that portion of the second ground pattern 360 which is exposed to the channels 611 to 618, the distal end portion 326 exposed to the channels 616 and 617, and the first electrode 322 exposed to the channel 613. Through such use of platinum, resistance to oxidation can be improved for the electrode.

A fifth ceramic layer 390 is disposed on the back side with respect to the heater pattern 380. The fifth ceramic layer 390 has a substantially rectangular outline which matches the fourth ceramic layer 370 when projected in the Y-axis direction. The heater pattern 380 is covered with the fifth ceramic layer 390. That is, the heater pattern 380 is sandwiched between and thus covered with the fourth ceramic layer 370 and the fifth ceramic layer 390. As a result, the heater pattern 380 is not exposed to the channels 611 to 618 and to the exterior of the sensor unit 300.

The first to fifth ceramic layers 310, 330, 350, 370, and 390 are formed of insulating ceramic (e.g., alumina). A structure composed of the first to fifth ceramic layers 310, 330, 350, 370, and 390 corresponds to the "structure" appearing in the "MEANS FOR SOLVING THE PROBLEM" section. A structure ST is shown in FIG. 6. The outside of the structure ST is the "exterior" of the sensor unit 300.

The fifth ceramic layer 390 has two vias 390v1 and two vias 390v2 at such positions as to be superimposed on two rear end portions 382 and 384, respectively, of the heater pattern 380 when projected in the Y-axis direction. The vias 390v1 and 390v2 extend through the fifth ceramic layer 390. The vias 390v1 and 390v2 are filled with electrically conductive members, respectively. The electrically conductive members electrically communicate with the two rear end portions 382, 384, respectively, of the heater pattern 380. An electrode pad 392 is provided on the back side of the fifth ceramic layer 390 and electrically communicates with the vias 390v1. Similarly, an electrode pad 394 is provided on the back side of the fifth ceramic layer 390 and electrically communicates with the vias 390v2.

The terminal 125t connected to the insulated electric wire 125 is in contact with the electrode pad 392 (see the lower left region in FIG. 4). The terminal 126t connected to the insulated electric wire 126 is in contact with the electrode pad 394 (see the middle region in FIG. 2 and the lower left region in FIG. 4). The heater pattern 380 is supplied with electric power from the electric circuit unit 112 (see FIG. 1(B)) through the insulated electric wire 125, the terminal 125t, the electrode pad 392, the vias 390v1, the insulated electric wire 126, the terminal 126t, and the vias 390v2.

In a state in which the sensor unit 300 is incorporated in the particulate sensor 100, the electrode pads 392 and 394 are located rearward of the metallic shell 503 and the second ceramic ring 507 (see the middle right region in FIG. 4 and the middle region in FIG. 3). Thus, the electrode pads 392 and 394 are in noncontact with exhaust gas.

As mentioned above, the heater pattern 380 heats the entire sensor unit 300 to a temperature of 550 to 600 degrees. Thus, for example, upon adhesion of a water droplet contained in exhaust gas to the third ceramic layer 350 and the fifth ceramic layer 390 which are exposed at the surface of the sensor unit 300, the third ceramic layer 350 and the fifth ceramic layer 390 may possibly be damaged by thermal shock.

However, in the present embodiment, the sensor unit 300 is covered with the protector 501 in the exhaust gas pipe 415 (see FIG. 1(B) and FIGS. 2 and 3). Also, that portion of the portion 300e in contact with exhaust gas flowing through the exhaust gas pipe 415 which is located at a position corresponding to the exterior of the exhaust gas pipe 415 is covered with the protector 501 and with a forward end portion of the metallic shell 503. Thus, the possibility of direct adhesion of a water droplet to the sensor unit 300 is low. Therefore, the possibility of occurrence of the above-mentioned situation can be reduced. Notable, the protector 501 has communication holes. Thus, the sensor unit 300 can receive exhaust gas which has passed through the communication holes of the protector 501.

The first ceramic layer 310 shown at the center of FIG. 6 has a plurality of vias 310v along the sides of the substantially rectangular overall outline of the outer peripheral portions 312 and 314 at such positions as to be superimposed on the first ground pattern 340 and the second ground pattern 360 when projected in the Y-axis direction. The plurality of vias 310v are disposed at such positions as to surround the channels 611 to 618, the discharge pattern 320, and the trap pattern 325. The vias 310v extend through the first ceramic layer 310.

Also, the second ceramic layer 330 has a plurality of vias 330v3 along the sides of its substantially rectangular outline at such positions as to align with the respective vias 310v of the first ceramic layer 310 when projected in the Y-axis direction. The vias 330v3 extend through the second ceramic layer 330.

The vias 310v of the first ceramic layer 310 and the vias 330v3 of the second ceramic layer 330 are filled with electrically conductive members, respectively. The electrically conductive members electrically communicate with the first ground pattern 340 and with the second ground pattern 360.

The discharge pattern 320 and the trap pattern 325 are surrounded by the first ground pattern 340 and the second ground pattern 360 as well as those electrically conductive members in the plurality of vias 310v and 330v3 which connect the first and second ground patterns 340 and 360. As will be described later, the first and second ground patterns 340 and 360 as well as the electrically conductive members in the plurality of vias 310v and 330v3 have an electric potential corresponding to the amount of ions not used for electrically charging soot. As will be described later, the electric potential is a reference electric potential in the sensor unit 300. As a result, the first and second ground patterns 340 and 360 and those electrically conductive members in the plurality of vias 310v and 330v3 which connect the first and second ground patterns 340 and 360 function as a Faraday cage for the discharge pattern 320 and the trap pattern 325. That is, the discharge pattern 320 and the trap pattern 325 are shielded from an external electric field. As a result, the discharge pattern 320 and the trap pattern 325 are free from variation in electric potential which is otherwise caused by external noise, and thus can function accurately.

The second ground pattern 360 and the first ground pattern 340 as well as those electrically conductive members in the plurality of vias 310v and 330v3 which connect the first ground pattern 340 and the second ground pattern 360 collectively function as the "sensor ground section" appearing in the "MEANS FOR SOLVING THE PROBLEM" section. A sensor ground section SG is shown in FIG. 6. The electric potential of the second ground pattern 360 and the first ground pattern 340 as well as those electrically conductive members in the plurality of vias 310v and 330v3 which connect the first ground pattern 340 and the second ground pattern 360 corresponds to the "first floating potential."

A2. Function of Particulate Sensor

Figure 7:
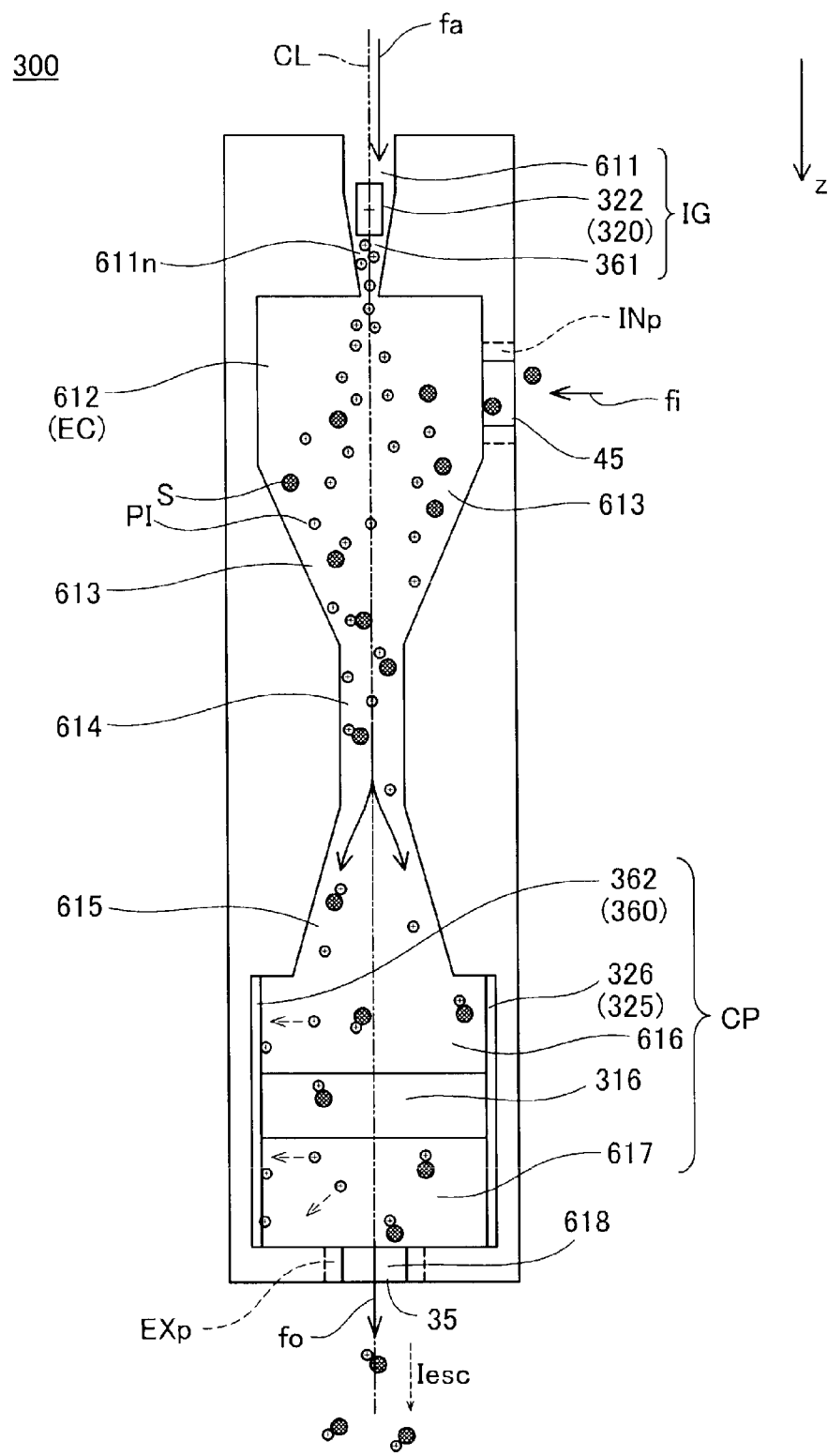
FIG. 7 Schematic view for explaining the function of a sensor unit for detecting the amount of particulates in exhaust gas.

FIG. 7 is a schematic view for explaining the function of the sensor unit 300 for detecting the amount of particulates in exhaust gas. FIG. 7 schematically illustrates the internal structure of the sensor unit 300 inserted into the exhaust gas pipe 415. However, in FIG. 7, in order to facilitate technical understanding, the disposition of components particularly in the x-axis and y-axis directions does not reflect actual conditions.

The sensor unit 300 has the channels 611 to 618 from the upstream side corresponding to the rear side toward the downstream side corresponding to the forward side (see the middle region in FIG. 6). The channel 611 receives high-pressure air supplied from the air supply tube 123 (see the middle region in FIG. 2). In FIG. 7, an arrow fa indicates the flow of high-pressure air which the sensor unit 300 receives.

As shown in FIGS. 4, 6, and 7, the channel 612 is greater in cross section than the channel 611. In the channel 612, exhaust gas containing soot S supplied through the intake hole 45 (openings 330h, 340h, and 350h in FIG. 6) and high-pressure air supplied from the channel 611 are mixed. In FIG. 7, an arrow fi indicates the flow of exhaust gas introduced into the sensor unit 300.

The forward end portion 611n of the channel 611 reduces downstream in cross section (see the middle region in FIG. 6 and the upper region in FIG. 7) and is connected, at its forward end, to the channel 612 which is greater in cross-sectional area than the channel 611. The forward end portion 611n of the channel 611 functions as a nozzle.

The second ground pattern 360 is exposed to the bottom of the channel 611. In the channel 611, discharge is performed between that electrode portion 361 of the second ground pattern 360 which forms the bottom of the channel 611, and the distal end portion 322 (first electrode 322) of the discharge pattern 320. As a result of the discharge, positive ions PI are generated. The positive ions PI, together with high-pressure air, flow into the channel 612 from the channel 611. The positive ions PI generated at the forward end portion 611*n* of the channel 611 and exhaust gas introduced into the channel 612 through the intake hole 45 are mixed mainly in the channel 612. At the time of mixing, portion of the positive ions PI adhere to the soot S in exhaust gas and electrically charge the soot. The ions and charged soot, together with exhaust gas, sequentially flow through the channels 613, 614, and 615. Hereinafter, that electrode portion 361 of the second ground pattern 360 which forms the bottom of the forward end portion 611*n* of the channel 611 may be referred to as the "second electrode 361."

The channel 611, the electrode portion 361 (second electrode 361) of the second ground pattern 360, and the distal end portion 322 (first electrode 322) of the discharge pattern 320 collectively function as the "ion generation section" appearing in the "MEANS FOR SOLVING THE PROBLEM" section. The electric potential of the first electrode 322 of the discharge pattern 320 corresponds to the "second floating potential." An ion generation section IG is shown in FIG. 7.

Also, the portion 323 other than the distal end portion 322 of the discharge pattern 320 corresponds to the "discharge potential portion" appearing in the "MEANS FOR SOLVING THE PROBLEM" section. The channel 612 functions as the "electric charge section" appearing in the "MEANS FOR SOLVING THE PROBLEM" section. The electric charge section EC is shown in FIG. 7.

The channels 616 and 617 are greater in cross section than the channels 614 and 615. As mentioned above, the second ground pattern 360 is exposed to the bottoms of the channels 616 and 617 (see the middle region in FIG. 6). The distal end portion 326 of the trap pattern 325 is exposed to the tops of the channels 616 and 617. The columnar portion 316 is disposed at the connection between the channels 616 and 617 and between the second ground pattern 360 which serves as a channel bottom, and the distal end portion 326 which serves as a channel top. The channel 614 and the columnar portion 316 are disposed at positions which include the imaginary center axis CL of the particulate sensor 100 (see the middle region in FIG. 6).

The electric circuit unit 112 imparts an electric potential higher than that of the second ground pattern 360 to the distal end portion 326 of the trap pattern 325 through the insulated electric wire 122. Thus, positive ions and soot electrically charged through adhesion of positive ions receive repulsion from the distal end portion 326 of the trap pattern 325. As a result, positive ions, which are small in mass, are diverted toward the bottom side and thus trapped by the second ground pattern 360 which faces the distal end portion 326. That portion of the second ground pattern 360 which faces the distal end portion 326 of the trap pattern 325 is indicated as a trapping region 362 in FIGS. 6 and 7.

Meanwhile, electrically charged soot is large in mass and is thus small in the degree of diversion caused by repulsion from the distal end portion 326. Accordingly, electrically charged soot is not trapped in the trapping region 362 and is discharged, as it is, to the exterior of the sensor unit 300 through the channel 618 and the discharge hole 35. In FIG. 7, an arrow fo indicates the flow of exhaust gas discharged from the sensor unit 300.

The columnar portion 316 is disposed at the downstream front of the channel 614. Thus, exhaust gas and air which have passed the channels 613 to 615 do not flow directly toward the channels 617 and 618, but their flow is disturbed by the columnar portion 316. Therefore, according to the present embodiment, positive ions can be efficiently trapped in the trapping region 362 as compared with a mode in which the columnar portion 316 is not provided, and exhaust gas and air which have passed the channels 613 to 615 flow directly toward the downstream channels 617 and 618.

The channels 616 and 617, the columnar portion 316, the distal end portion 326 of the trap pattern 325, and the trapping region 362 collectively function as the "capture section" appearing in the "MEANS FOR SOLVING THE PROBLEM" section. A capture section CP is shown in FIG. 7.

Figure 8:
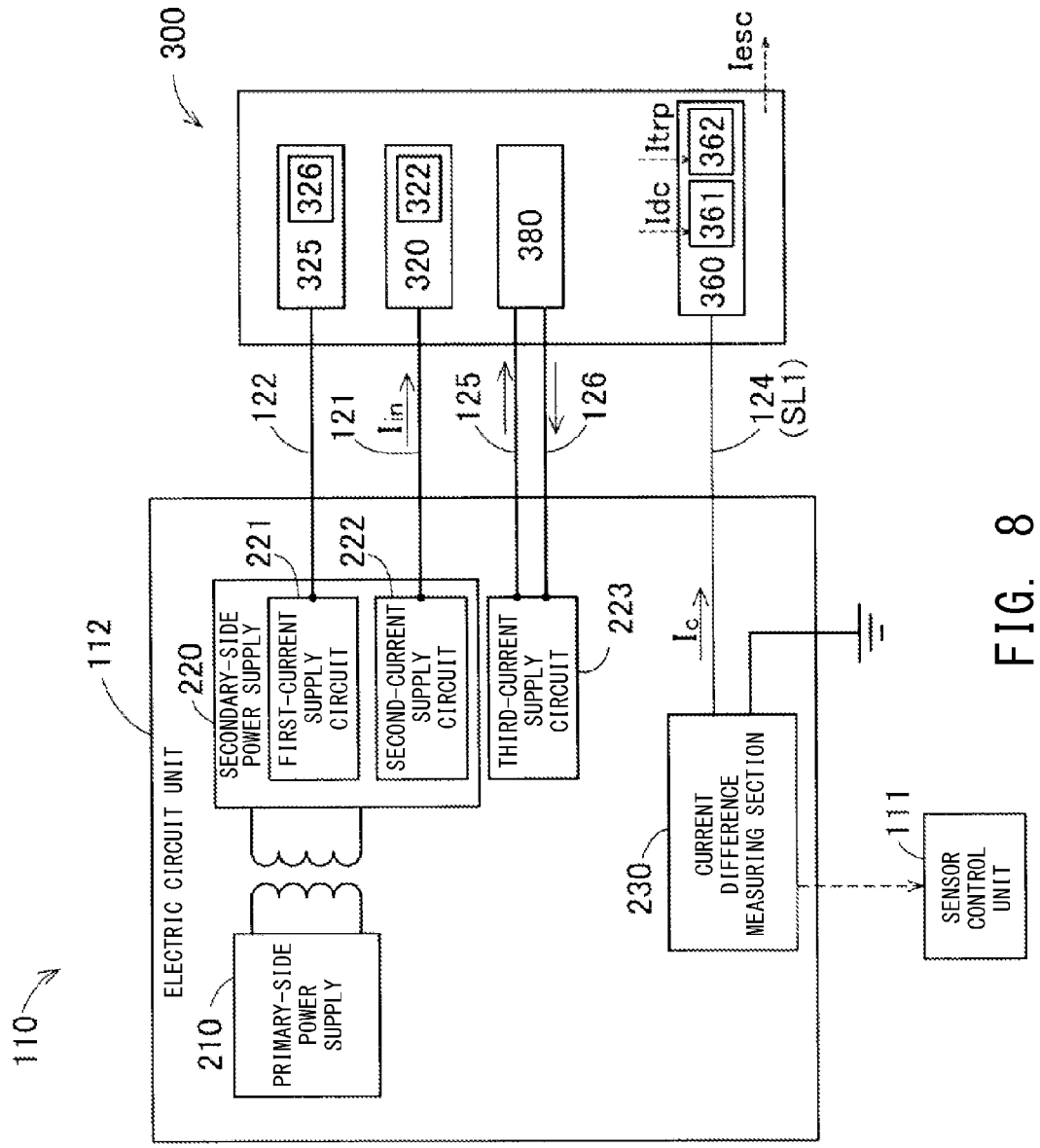
FIG. 8 Block diagram for explaining the operation of a sensor control unit 111 of detecting the amount of soot in exhaust gas by use of a particulate sensor 100.

FIG. 8 is a block diagram for explaining the operation of the sensor control unit 111 of detecting the amount of soot in exhaust gas by use of the particulate sensor 100. The electric circuit unit 112 includes a primary-side power supply 210, a secondary-side power supply 220, a third-current supply circuit 223, and a current difference measuring section 230. The primary-side power supply 210 supplies high-voltage power to the secondary-side power supply 220 through a transformer under instruction from the sensor control unit 111 (see FIG. 1(B)). The secondary-side power supply 220 includes a first-current supply circuit 221 and a second-current supply circuit 222.

The first-current supply circuit 221 is connected the distal end portion 326 of the trap pattern 325 (see the middle region in FIG. 6 and the lower region in FIG. 7) through the second insulated electric wire 122. The distal end portion 326 of the trap pattern 325 is supplied with electric power (100 V) from the first-current supply circuit 221 for applying repulsion to the positive ions PI.

The second-current supply circuit 222 is connected to the first electrode 322 of the discharge pattern 320 (see the middle region in FIG. 6 and the upper region in FIG. 7) through the first insulated electric wire 121. The first electrode 322 is supplied with electric power (2 kV to 3 kV, 100 kHz) from the second-current supply circuit 222 for generating corona discharge. The second-current supply circuit 222 is a constant current circuit and supplies, for corona discharge, a fixed current $I_{in}$ of, for example, about 5 µA to the first electrode 322 of the discharge pattern 320.

The third-current supply circuit 223 is connected to the heater pattern 380 (see the upper left region in FIG. 6) through the third and fourth insulated electric wires 125 and 126, etc. The heater pattern 380 is supplied with electric power from the third-current supply circuit 223 for increasing the temperature of the sensor unit 300. A circuit composed of the third-current supply circuit 223, the third and fourth insulated electric wires 125 and 126, and the heater pattern 380 is independent of the discharge pattern 320, the trap pattern 325, and the second ground pattern 360.

The current difference measuring section 230 is electrically connected to the trapping region 362 (the trapping region 362 connected to the second ground pattern 360) through the signal line 124 (first shield line SL1), etc. The current difference measuring section 230 is grounded through the exhaust gas pipe 415 or the chassis of the vehicle 490.

When the input current $I_{in}$ flows from the second-current supply circuit 222 to the first electrode 322 of the discharge pattern 320, as a result of corona discharge, a discharge current $I_{dc}$ flows from the first electrode 322 to the second ground pattern 360 through the second electrode 361, and the positive ions PI are generated. As shown in FIG. 7, portion of the positive ions PI are used for electrically charging the soot S, and the remaining positive ions PI not used for electrically charging the soot S are trapped in the trapping region 362.

Current corresponding to a flow of the positive ions PI used for electrically charging the soot S and escaping to the exterior of the sensor unit 300 is called the "escaping current $I_{esc}$." Current corresponding to a flow of the positive ions PI to be trapped in the trapping region 362 is called the "trap current $I_{trp}$." For the four currents $I_{in}$, $I_{dc}$, $I_{esc}$, and $I_{trp}$ which flow as a result of corona discharge, the following relational expression (1) holds.

$$I_{in} = I_{dc} + I_{trp} + I_{esc} \quad (1)$$

Of these currents, the discharge current $I_{dc}$ and the trap current $I_{trp}$ flow to the second ground pattern 360. As mentioned above, the input current $I_{in}$ to the first electrode 322 of the discharge pattern 320 is controlled at a fixed value by the second-current supply circuit 222. Therefore, the escaping current $I_{esc}$ can be obtained by calculating the difference between the input current $I_{in}$ and the sum of the two currents $I_{dc}$ and $I_{trp}$ flowing to the second ground pattern 360 (the following expression (2)).

$$I_{esc} = I_{in} - (I_{dc} + I_{trp}) \quad (2)$$

In the second ground pattern 360, an electric potential thereof drops from the external reference electric potential (electric potential of the chassis of the vehicle 490) by a value corresponding to the escaping current $I_{esc}$ by which the input current $I_{in}$ is reduced. By contrast, a compensation current $I_c$ flows from the current difference measuring section 230 to the signal line 124 for compensating the drop in electric potential. The compensation current $I_c$ corresponds to the escaping current $I_{esc}$. The current difference measuring section 230 sends a measured value of the compensation current $I_c$ to the sensor control unit 111 as a measured value of the escaping current $I_{esc}$.

The escaping current $I_{esc}$ is correlated with the amount of the positive ions PI used for electrically charging the soot S (see the lower region in FIG. 7). The amount of the positive ions PI used for electrically charging the soot S is correlated with the amount of the soot S per unit flow rate in exhaust gas. Therefore, by means of measuring (detecting) the escaping current $I_{esc}$ as mentioned above, the amount of the soot S per unit flow rate in exhaust gas can be obtained. The sensor control unit 111 obtains the amount of the soot S in exhaust gas from the escaping current $I_{esc}$ detected by the current difference measuring section 230, by use of a map, arithmetic expressions, etc., which have been stored beforehand.

In this manner, the sensor control unit 111 detects the amount of the soot S in exhaust gas on the basis of the amount of current which flows to the second ground pattern 360, stemming from the electric potential of the second ground pattern 360 which varies with the amount of the positive ions PI used for electrically charging the soot S and escaping to the exterior of the sensor unit 300. In other words, the sensor control unit 111 can also be said to detect the amount of the soot S in exhaust gas on the basis of the amount of current which flows to the second ground pattern 360, stemming from the electric potential of the second ground pattern 360 which varies with the amount of the positive ions PI not used for electrically charging the soot S and trapped in the trapping region 362 (connected to the second ground pattern 360).

In the present embodiment, the discharge pattern 320 and the trap pattern 325 are surrounded by the first ground pattern 340 and the second ground pattern 360 as well as those electrically conductive members in the plurality of vias 310$v$ and 330$v$3 which connect the first and second ground patterns 340 and 360. Thus, current which leaks from the discharge pattern 320 and the trap pattern 325 flows to the first ground pattern 340 and the second ground pattern 360 as well as those electrically conductive members in the plurality of vias 310$v$ and 330$v$3 which connect the first and second ground patterns 340 and 360. Therefore, even though the discharge current $I_{dc}$ flowing from the first electrode 322 to the second electrode 361 contains an error stemming from the current leakage, the error is absorbed by the trap current $I_{trp}$ in the second ground pattern 360. Thus, even though current leaks from the discharge pattern 320 and the trap pattern 325, an error contained in the right side of expression (2) becomes very small or zero. Therefore, the escaping current $I_{esc}$ obtained from expression (2) is accurate. As a result, an output value from the particulate sensor 100 is accurate.

The particulate sensor 100 of the present embodiment can detect the amount of particulates such as the soot S contained in exhaust gas emitted from the internal combustion engine 400 through a simple, small-sized configuration.

B. Modifications

The present invention is not limited to the above-described embodiment or mode, but may be embodied in various other forms without departing from the gist of the invention. For example, the following modifications are also possible.

B1. Modification 1

In the embodiment described above, air is used for leading the ions PI generated in the ion generation section IG to the electric charge section EC and the capture section CP. However, gas utilized for leading the ions PI to the electric charge section EC and the ion capture section CP can be another gas which does not contain particulates to be detected. Preferably, gas utilized for leading the ions PI to the electric charge section EC and the capture section CP is unlikely to be ionized in an environment where the particulate sensor 100 is used. More preferably, gas utilized for leading the ions PI to the electric charge section EC and the capture section CP is ionized through corona discharge. Furthermore, preferably, the gas exists around the particulate sensor 100 and the sensor drive unit 110 in an environment where the particulate sensor 100 is used.

B2. Modification 2

In the embodiment described above, a nozzle is formed at the forward end portion 611$n$ of the channel 611 in the sensor unit 300. However, a nozzle may not be formed in the channel in the sensor unit 300. However, through provision of a nozzle, a jet stream from the nozzle can generate negative pressure in a downstream space. Through provision of the intake hole 45 in a wall of the space located downstream of the nozzle, exhaust gas can be efficiently taken in from outside.

B3. Modification 3

In the embodiment described above, positive ions are generated, through corona discharge, between the first electrode 322 of the discharge pattern 320 and the second electrode 361 of the second ground pattern 360, and the distal end portion 326 of the trap pattern 325 generates repulsion toward the positive ions; however, the present invention is not limited thereto. For example, the amount of particulates contained in gas to be detected may be detected through employment of the following configuration: the first electrode 322 and the second electrode 361 are changed in positive and negative connections so as to reverse polarity of the trap pattern 325 for generating negative ions through corona discharge, and the distal end portion 326 of the trap pattern 325 generates repulsion toward the negative ions.

More specifically, in the embodiment described above, the electric potential of the first electrode 322 of the discharge pattern 320 as the second floating potential is 2 kV to 3 kV higher than the electric potential of the sensor ground section SG as the first floating potential. The second electrode 361 is connected to the sensor ground section SG. However, the second floating potential which is the electric potential of one of two electrodes for generating ions can be lower than the first floating potential. The electric potential of the other electrode for generating ions can be higher than the second floating potential and can also be lower than the second floating potential. However, preferably, the electric potential of the other electrode for generating ions is the first floating potential.

B4. Modification 4

In the embodiment described above, in the ion generation section IG, a voltage of 2 kV to 3 kV is intermittently applied at 100 kHz to the first electrode 322. However, another voltage may be applied at another frequency to the electrodes for generating ions. However, in a mode of intermittent application of voltage or application of another AC voltage, deterioration in coating of insulated electric wires is of particular note. Thus, application of the present invention to such a mode is particularly preferred.

B5. Modification 5

In the embodiment described above, the portion 323 other than the distal end portion 322 of the discharge pattern 320, the portion 327 other than the distal end portion 326 of the trap pattern 325, the first ground pattern 340, the vias 310v of the first ceramic layer 310, and the vias 330v3 of the second ceramic layer 330 are provided in the interior of the structure ST made of insulating ceramic. However, electrically conductive members in regions in noncontact with gas which contains particulates to be detected may be exposed to the exterior of the structure.

B6. Modification 6

In the embodiment described above, the vias 310v of the first ceramic layer 310 and the vias 330v of the second ceramic layer 330 are provided along three sides of the rectangular cross section of the structure ST of the sensor unit 300. The first ground pattern 340 forms a plane perpendicular to the vias 310v and 330v in the interior of the rectangular columnar structure ST. In the embodiment described above, these members constitute the sensor ground section SG and form a Faraday cage which surrounds the discharge pattern 320 and the trap pattern 325. That is, the members which constitute the sensor ground section SG are disposed on the X-axis positive and negative sides, on the Y-axis negative side, and on the Z-axis negative side with respect to the discharge pattern 320 and the trap pattern 325.

However, the sensor ground section which surrounds the portion 323 of the discharge pattern 320 serving as the discharge potential portion may assume another configuration. However, preferably, the sensor ground section is configured as follows: when a closed space is formed by connecting component members of the sensor ground section by means of planes, the first electrode and the discharge potential portion are located within the closed space.

B7. Modification 7

In the embodiment described above, the columnar portion 316 is disposed at the connection between the channel 616 and the channel 617 and extends from the bottoms of the channels to the ceilings of the channels. However, another shape and structure may be employed for hindering a rectilinear flow of gas in a channel and for promoting trapping of ions. For example, in order to hinder a rectilinear flow of gas in a channel, a slope is formed at the bottom of a channel in such a manner as not to reach the ceiling of the channel. Also, a plate-like structure may be disposed in a channel.

B8. Modification 8

In the embodiment described above, the heater pattern 380 heats the entire sensor unit 300 to a temperature of 550 to 600 degrees. However, no particular limitation is imposed on the heater so long as the heater can heat electrically conductive members in contact with gas which contains particulates to be detected, to such a temperature as to burn particulates and other impurities adhering to the electrically conductive members. The heating temperature may be determined according to materials for the electrically conductive members in contact with gas, and compositions of particulates and other impurities adhering to the electrically conductive members.

The heater may not be a single heater, but may be composed of a plurality of heaters which can heat any one of or any combination of the first and second electrodes, the capture section, and the electric charge section.

B9. Modification 9

In the embodiment described above, the ion generation section IG, the electric charge section EC, and the capture section CP are disposed in the sensor unit 300 of the particulate sensor 100, which unit is disposed within the exhaust gas pipe 415. However, the sensor unit may be provided only with the electric charge section EC and the capture section CP. For example, the ion generation section IG may be provided isolatedly in that region of the particulate sensor 100 which is located externally of the exhaust gas pipe 415.

DESCRIPTION OF REFERENCE NUMERALS AND SYMBOLS

35: discharge hole
45: intake hole
100: particulate sensor
110: sensor drive unit
111: sensor control unit
112: electric circuit unit
113: air supply unit
120: cable
1201: glass fiber filler
1202: first cable coating layer
1203: second cable coating layer
1204: covering 120e: cable end surface
121, 122, 125, 126: insulated electric wire
1210, 1220, 1250, 1260: core wire
1211, 1221, 1251, 1261: resin coating layer
121t, 122t, 125t, 126t: terminal
123: air supply tube
123s: reinforcement member
124: signal line
124t: terminal
210: primary-side power supply
220: secondary-side power supply
221: first-current supply circuit
222: second-current supply circuit
223: third-current supply circuit
230: current difference measuring section
300: sensor unit
310: first ceramic layer
310v: via
312, 314: outer circumferential portion
316: columnar portion
320: discharge pattern
322: distal end portion (first electrode) of discharge pattern
323: portion other than distal end portion of discharge pattern
324: rear end portion of discharge pattern
325: trap pattern
326: distal end portion of trap pattern
327: portion other than distal end portion of trap pattern
328: rear end portion of trap pattern
330: second ceramic layer
330h, 340h, 350h: opening
330v1 to 330v3: via
340: first ground pattern
342, 344: opening
350: third ceramic layer
350v1 to 350v2: via
352: electrode pad
354: electrode pad
356: electrode pad
360: second ground pattern
361: electrode portion (second electrode) of second ground pattern
362: trap
370: fourth ceramic layer
380: heater pattern
382, 384: rear end portion of heater pattern
390: ceramic layer
390v1, 390v2: via
392: electrode pad
394: electrode pad
400: internal combustion engine
410: fuel supply unit
411: fuel pipe
415: exhaust gas pipe
416: filter device
417: attachment boss
420: vehicle control unit
490: vehicle
501: protector
502: gasket
503: metallic shell
504: sheet packing
505: first ceramic ring
506: talc
507: second ceramic ring
508: line packing
509: inner tube
509c: crimped portion
510: separator
510h: through hole
511: grommet
512: outer tube
512c: crimped portion
611 to 618: channel
CL: imaginary center axis
CP: capture section
DL: extending direction of exhaust gas pipe
EC: electric charge section
F: arrow for indicating flow of exhaust gas
$I_c$: compensation current
$I_{dc}$: discharge current
$I_{esc}$: escaping current
$I_{in}$: input current
$I_{trp}$: trap current
IG: ion generation section
PI: positive ion
S: particulate (soot)
SG: sensor ground section
SL1: first shield line
SL2: second shield line
fa: arrow for indicating flow of air
fi: arrow for indicating flow of exhaust gas to be introduced into sensor unit
fo: arrow for indicating flow of exhaust gas discharged from sensor unit

The invention claimed is:

1. A particulate sensor attached to a pipe having electrical conductivity, and adapted to detect the amount of particulates in gas flowing through the pipe, comprising a sensor unit, wherein
the sensor unit comprises
an ion generation section for generating ions,
an electric charge section for electrically charging at least portion of the particulates in the gas which contains the particulates, by use of the ions,
a capture section for trapping at least portion of the ions not used for electrically charging the particulates, and
a sensor ground section connected to the capture section and having a first floating potential corresponding to the amount of the ions trapped by the capture section;
the sensor unit can detect the amount of the particulates in the gas on the basis of electric potential of the sensor ground section; and
the sensor ground section is covered with insulating ceramic at an outer portion of the sensor unit which comes into contact with the gas,
wherein
the ion generation section comprises a first electrode having a second floating potential different from the first floating potential, and a second electrode connected to the sensor ground section and having the first floating potential;
the ion generation section generates the ions by producing discharge between the first electrode and the second electrode;
the sensor unit further comprises a discharge potential portion connected to the first electrode and having the second floating potential; and
the sensor ground section surrounds the first electrode and the discharge potential portion.

2. The particulate sensor according to claim 1, comprising
a structure formed of insulating ceramic and having the ion generation section, the electric charge section, the capture section, the sensor ground section, and the discharge potential portion, wherein the discharge potential portion is covered with the insulating ceramic used to form the structure; and the electric charge section is provided by the insulating ceramic used to form the structure.

3. The particulate sensor according to claim 2, wherein the sensor unit further comprises a heater for heating the first and second electrodes and the capture section to a temperature capable of burning the particulates at the first and second electrodes and the capture section.

4. The particulate sensor according to claim 2, wherein the sensor unit further comprises a heater for heating the electric charge section to a temperature capable of burning the particulates at the electric charge section.

5. The particulate sensor according to claim 3, further comprising a protector surrounding the outer portion of the structure which comes into contact with the gas, and allowing the gas which contains the particulates to pass therethrough.

6. The particulate sensor according to claim 4, further comprising a protector surrounding that outer portion of the structure which comes into contact with the gas, and allowing the gas which contains the particulates to pass therethrough.

* * * * *